United States Patent [19]

Sato et al.

[11] 4,060,597

[45] Nov. 29, 1977

[54] SEROLOGICAL REAGENT AND PREPARATION THEREOF

[75] Inventors: Yukio Sato; Seijun Wada, both of Osaka; Shigetaka Matsuzawa, Tokyo, all of Japan

[73] Assignee: Takeda Chemical Industries, Ltd., Osaka, Japan

[21] Appl. No.: 593,531

[22] Filed: July 7, 1975

[30] Foreign Application Priority Data

July 8, 1974 Japan .................................. 49-78604

[51] Int. Cl.$^2$ ..................... G01N 31/00; G01N 31/06; G01N 33/16
[52] U.S. Cl. .................................... 424/12; 23/230 B; 23/253 TP; 424/8; 424/13; 424/78; 424/81
[58] Field of Search .................. 424/8, 12, 13, 78, 81; 23/230 B, 253 TP; 260/29.7 NR, 29.6 PM, 29.6 ME, 8

[56] References Cited

U.S. PATENT DOCUMENTS

| | | | |
|---|---|---|---|
| 3,244,657 | 4/1966 | Grosser | 260/29.6 ME |
| 3,422,049 | 1/1969 | McClain | 260/29.6 PM |
| 3,547,847 | 12/1970 | Levine | 260/8 |
| 3,551,555 | 12/1970 | Schuurs | 424/12 |
| 3,749,690 | 7/1973 | Patella | 260/8 |

FOREIGN PATENT DOCUMENTS 885,604  12/1961  United Kingdom ..... 260/29.6 EME

OTHER PUBLICATIONS

Van Oss, J. of The Reticuloendothelial Soc. vol. 3, 1966, pp. 29–40.

Primary Examiner—Albert T. Meyers
Assistant Examiner—A. P. Fagelson
Attorney, Agent, or Firm—Wenderoth, Lind & Ponack

[57] ABSTRACT

A latex reagent is prepared by allowing latex particles to adsorb a nonionic surfactant of ethylene oxide type, sensitizing the latex particles thus having the surfactant adsorbed with a serologically active substance such as antigen or antibody and suspending the sensitized latex particles in an aqueous solvent. The thus-prepared latex reagent has an excellent quality, e.g. both a high stability and a high sensitivity in serologic reactions, and can be employed with advantages in a broad variety of serologic reactions.

14 Claims, No Drawings

SEROLOGICAL REAGENT AND PREPARATION THEREOF

The present invention relates to an improvement of latex reagents for serologic reactions.

To detect antigenic substances such as bacteria or viruses or their decomposition products and the antibodies to them is an extremely important procedure for the diagnosis of diseases, and tests are performed by a variety of techniques which can be classified into such major categories as agglutination reactions (including agglutination-inhibition reactions), sedimentation reactions, complement fixation reactions and so on.

Australia antigen (also known as "hepatitis-associated antigen"), in particular, occurs in the human sera infected with transfusion-associated hepatitis virus and is considered to be the transfusion-associated hepatitis virus or a substance closely associated with said virus. Thus, various tests have been developed because detection of this antigen is not only a procedure indispensable to the prophylaxis of transfusion-associated hepatitis but is extremely effective in the prognosis of hepatitic patients and the evaluation of therapeutic effects.

Another example is the use for detection of rheumatoid factor. A patient with chronic rheumatoid arthritis, which is a typical auto-immune disease, produces rheumatoid factor which is an auto-antibody to human immunoglobulin G (hereinafter immunoglobulin G will be referred to as IgG). As by detecting this rheumatoid factor chronic rheumatoid arthritis can be diagnosed, there have been hitherto proposed many tests such as Waaler-Rose Test, Heller's Modified Test and the agglutination of human Ig G-sensitized latex particles, in all which the presence of rheumatoid factor in subject sera is examined by means of agglutination reaction.

Among these tests for various antigens and antibodies, the agglutination-reaction (including agglutination-inhibition reaction) techniques involving the use of a particulate carrier having some serologically active substance, e.g. an antigen or an antibody, adsorbed thereon are expedient and sensitive methods and have been in common usage. As the particulate carriers that are in use, there may be mentioned, among others, human and animal erythrocytes and other cells, microbial cells, collodion particles, kaolin, bentonite, activated carbon, cellulose derivatives, latex particles (e.g. particles of natural rubber or synthetic rubber latex, polystyrene latex, polyvinyltoluene latex) and so on. However, many of them have only limited ranges of applications as there are involved many such factors as the capacity of carriers to adsorb serologically active substances, the shelf-lives of carriers, sensitivity and, when cells are used, the death or spoilage of cells, to name but a few factors. Polystyrene latex, being a synthetic product, has a longer shelf-life than other carriers and, moreover, notwithstanding the fact that it securely binds proteins and others, the antigenic properties of the bound proteins, etc. are substantially not impaired. Because of these desirable properties discovered in polystyrene latex, it has been employed as a raw material for a large variety of serological clinical test reagents.

According to the production method employed, polystyrene latex varies in colloid-chemical properties and in behavior during serological reactions, and whereas the polystyrene latex provided with excessive colloid-chemical stability does not cause serological agglutination reactions any longer, an unstable latex undergoes spontaneous agglutination non-specifically so that it cannot be used as a serologic reagent.

Owing to these problems, considerable difficulty is encountered in the preparation of a polystyrene latex suited for serologic reactions and the conventional polystyrene latices for serological reactions are known to have the following disadvantages.

1. The latices sensitized with various antigens or antibodies often tend to undergo spontaneous agglutination during storage.
2. Even when a latex is of the type which does not undergo spontaneous agglutination during storage, it sometimes undergoes a nonspecific agglutination upon admixture with the serum to be tested, leading to erroneous diagnosis.
3. Even when a serologic agglutination reaction ought to be negative, there are cases in which a spontaneous agglutination of latex is involved to a certain extent so that the latex may give a somewhat coarse appearance, with the result that in tests such as a potency assay, the assessment of results is sometimes rendered difficult.

It is thought that should improvements be realized in the foregoing aspects, it would be possible to improve the performances of serological diagnostic reagents prepared from polystyrene latex particles and, at the same time, to develop new testing methods. However, if it be contemplated to eliminate the above disadvantages by adding to the colloid-chemical stability of polystyrene latex, serologic agglutination reactions will be suppressed. Stated differently, the property of a reagent to exhibit a serologically sensitive reaction is a property which is inherently in conflict with its colloid-chemical stability and, therefore, it has been considered to be extremely difficult to simultaneously satisfy the two requirements.

Under the above technical situation, the present inventors have unexpectedly found that a superior latex reagent for serologic reactions which is free from the aforementioned disadvantages can be obtained by allowing latex particles to adsorb a surfactant of a specific type, i.e. a nonionic surfactant of ethylene oxide type, sensitizing the latex particles thus having the surfactant adsorbed with a serologically active substance e.g. antigen or antibody and suspending the sensitized latex particles in an aqueous solvent.

Thus, the principal object of the present invention is to provide a latex reagent for serologic reaction which is improved in its quality. Another object is to provide a method for preparing the said improved latex reagent. A further object is to provide a basal latex for serologic reactions which is improved in its quality. Other objects will be made clear from the description and claims hereinafter.

The said objects are realized by subjecting the particles of a latex to a particular sequence of steps, i.e. allowing the latex particles to absorb a nonionic surfactant of ethylene oxide type, sensitizing the latex particles thus having the surfactant adsorbed with a serologically active substance and suspending the sensitized latex particles in an aqueous solvent.

According to the present invention use may be made, as the raw latices, of any latices which are employable for preparing the latex reagents for serologic reactions. As examples of such raw latices, there may be mentioned natural rubber latex and the latices of synthetic resins such as the homopolymers and copolymers of styrene or its derivatives (methylstyrene, ethylstyrene, chlorostyrene, etc.) olefins (e.g. ethylene, propylene, etc.), acrylic acid or its derivatives (methyl acrylate, ethyl acrylate, etc.), methacrylic acid or its derivatives (methyl methacrylate, ethyl methacrylate, acrylonitrile, acrylamide), dienes (butadiene, chloroprene, isoprene, etc.), vinyl chloride, vinylidene chloride, vinyl acetate and so on. Advantageous are the homopolymer or copolymer latices of styrene, chlorostyrene, methyl methacrylate, vinyl chloride and vinylidene chloride. Among these latices, homopolymers of chlorostyrene, vinyl chloride or vinylidene chloride and copolymers of them with other monomers (e.g. styrene) have a specific gravity similar to that of erythrocytes, i.e., of about 1.2 ± 0.05, and therefore, the latex reagent prepared from these latices according to the present invention can be employed for quantitative serologic reactions by the microtitration technique per se known, in addition to the qualitative serologic reaction.

Such a raw latex is in general advantageously employed in the particle diameter range from about 0.1 to about 1 micron, especially from about 0.3 to about 0.9 micron.

As the nonionic surfactant of ethylene oxide type there are employed with advantage block copolymers of ethylene oxide and polyoxypropylene glycol; polyoxyethylene alkyl ethers; polyoxyethylene alkylaryl ethers; and so on.

The aforementioned block copolymer of ethylene oxide and polyoxypropylene glycol can be obtained by ring-opening polymerization of ethylene oxide and polyoxypropylene glycol and shown by the following formula:

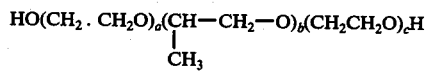

(wherein $b$ means a number within the range of from 16 to 66, and the sum of $a$ and $c$ falls within the range of from 2.5 to 282).

Of such block copolymers of ethylene oxide and polyoxypropylene glycol, those which contain, within their respective molecules, about 50% to about to 80%, especially about 65% to about 80%, of ethylene oxide, with the molecular weight of the hydrophobic polyoxypropylene glycol units being about 950 to about 3,850, are employed with particular advantage. As examples of the most advantageous block copolymers, there may be mentioned the commercially available block copolymers sold by Wyandotte Chemical Corporation, U.S.A., under the name of Pluronic F-38(ethylene oxide content is 80%, molecular weight of polyoxypropylene glycol is 950), Pluronic F-68 (ethylene oxide content is 80%; molecular weight of polyoxypropylene glycol is 1750), Pluronic F-77 (ethylene oxide content is 70%, molecular weight of polyoxypropylene is 2050), and so on.

As the aforementioned polyoxyethylene alkyl ethers, those containing alkyls of 12 to 18 carbon atoms are advantageous. Thus, polyoxyethylene lauryl ether, polyoxyethylene oleyl ether, polyoxyethylene cetyl ether, etc. may be mentioned by way of example. As the polyoxyethylene alkylaryl ethers, those containing phenyl substituted by alkyl of 8 to 18 carbon atoms are advantageous. Thus, for example, there may be mentioned polyoxyethylene octylphenyl ether, polyoxyethylene nonylphenyl ether, polyoxyethylene laurylphenyl ether and so on. Among these polyoxyethylene alkyl ethers and polyoxyethylene alkylaryl ethers, those containing about 30 to about 100 moles, especially about 30 to about 70 moles, of ethylene oxide within their respective molecules are employed with particular advantage. As examples of such ethers, there may be mentioned the commercially available preparations sold by Dai-ichi Kogyo Seiyaku, Japan, under the name of Emulsit 9 (polyoxyethylene nonylphenyl ether; 30 moles of ethylene oxide), Emulsit 25 (polyoxyethylene nonylphenyl ether; 50 moles of ethylene oxide), Emulsit 49 (polyoxyethylene nonylphenyl ether; 70 moles of ethylene oxide), Emulsit L 16 (an equal molar mixture of polyoxyethylene lauryl ether and polyoxyethylene myristyl ether; 40 moles of ethylene oxide), Emulsit L 36(an equal molar mixture of polyoxyethylene lauryl ether and polyoxyethylene myristyl ether; 60 moles of ethylene oxide), and so on.

The amount of the nonionic surfactant of ethylene oxide type to be adsorbed on latex particles can be appropriately selected according to the type of latex, the type of contemplated serologic reaction and other factors. Generally speaking, it is advantageous to have the nonionic surfactant of ethylene oxide type adsorbed in the proportion based on latex particles of about 0.00001 to about 5% by weight, particularly about 0.0001 to about 1% by weight and, for still better results, about 0.0001 to about 0.1% by weight.

In allowing the latex particles to adsorb such a nonionic surfactant of ethylene oxide type, it is advisable to contact the latex particles with said surfactant in an aqueous medium such as water.

For example, after a latex is prepared by emulsion polymerization or other suitable procedure in a concentration of about 5 to 10%, said surfactant is added and the mixture is kept standing at room temperature. After the adsorption of the surfactant has reached an equilibrium, the supernatant fluid is discarded and the latex particles are redispersed in an aqueous medium. If desired, this procedure may be repeated.

Alternatively, when a polymer latex is produced by emulsion polymerization which is one of the commonest methods, the aforementioned surfactant may be caused to become adsorbed on latex particles by adding the surfactant to the polymerization reaction system.

The thus-obtained basal latex, on whose particles a nonanionic surfactant of ethylene oxide type has been adsorbed displays superior stability as compared with the hitherto known diagnostic latices.

In accordance with the present invention, the latex particles on which a nonionic surfactant has been adsorbed in the above manner is then sensitized with a serologically active substance to prepare a latex reagent for serologic reactions. The serologically active substance may for example be any of the various antigens and antibodies that can be employed for agglutination, agglutination-inhibition and other serological reactions.

In sensitizing the latex particles with a serologically active substance, use may be made of a sensitizing technique that is conventional per se. It is advantageous to contact the latex particles with such a serologically active substance in an aqueous solvent such as water, physiological saline, a buffer solution of especially about pH 3.5 to 9.5 (e.g. glycine buffer, phosphate buffer, borate buffer, glycine-HCl buffer, glycine-NaCl buffer, glycine-NaOH buffer, etc.) or the like. Generally, this sensitization is accomplished by mixing a solution containing a serologically active substance with the basal latex and allowing the mixture to stand. If desired, however, the contacting time may be reduced by stirring or shaking. As examples of the aforementioned solution containing a serologically active substance, there may be mentioned the sera or plasmas containing such active substances and the suspensions of purified active substances. Especially, this sensitization treatment is advantageously carried out at pH about 7.0 to 8.6 and at a temperature of about 20° to 37° C. If desired, after the sensitization treatment the residual surfaces of the latex particles may be saturated with a substance which are capable of being adsorbed on the latex particles, such as bovine serum albumin, equine serum albumin and so on.

The latex particles thus sensitized are suspended, after being rinsed with an aqueous solvent if so desired, in an aqueous solvent. As the aqueous solvent, there may be advantageously employed water, a physiological saline, a buffer solution of especially pH about 3.5 to 9.5 (e.g. glycine buffer, phosphate buffer, borate buffer, glycine-HCl buffer, glycine-NaCl buffer, glycine-NaOH buffer, etc.) and the like. From the viewpoint of practical use for serologic reactions, it is generally advantageous to suspend the sensitized latex particles in an aqueous solvent so as to give a preparation containing the latex particles in an amount, at the use, of from about 0.1 to about 5% by volume, especially from about 0.5 to about 1%, relative to the whole preparation.

While thus-prepared latex reagent of the present invention is ready for use as it is, it may be supplemented with optional ingredient or ingredients such as antiseptics (e.g. sodium azide). The latex reagent of the present invention can be employed for agglutination, agglutination-inhibition and other serologic reactions by per se known techniques.

The latex reagent for serologic reactions of the present invention is essentially characterized by the following advantages compared with the hitherto known latex reagents for serologic reactions:

1. No spontaneous agglutination takes place even when sensitized with a fairly high concentration of a solution of a colloid-chemically unstable antigenic substance. This means that even a fairly weak antigen-antibody reaction can be detected with the latex reagent of this invention.

2. Because the present latex is stable even on the acidic side, serologic reactions in acidic buffers can be achieved. This fact indicates the possibility of testing antigen-antibody reaction systems of the kinds which cannot be tested with the conventional latex.

3. Compared with the known diagnostic polystyrene latex reagent, negative reaction images can be clearly detected. This fact indicates that the present latex reagent is free from the disadvantage of the known latex reagents that assessments as to the positivity-negativity of reactions may vary according to different testers.

4. The present latex is highly stable irrespective of whether it is before or after the sensitization with a serologically active substance. Therefore, there is no possibility for the tester to be misled by spontaneous agglutination or the latex reagent is made unserviceable thereby.

The following Examples are intended to show the advantages of the latex reagent of this invention in serologic reaction applications but it should be understood that these data are related to a limited part of the versatility of the reagent and that the reagent can be utilized in a large variety of serologic reactions.

Throughout the present specification as well as in claims, abbreviations "g.", "mg.", "ml.", "° C" and "r.p.m." respectively mean "gram(s)", "milligram(s)", "milliliter(s)", "degree(s) centigrade" and "revolution(s) per minute".

EXAMPLE 1

The production of the basal latices and the agglutination of the basal latices upon sensitization with human serum.

Basal Latices

Latex No. 1

Commercial unsensitized latex containing 1% by volume of polystyrene particles with an average particle diameter of 0.81 micron.

Latex No. 2

A reaction vessel was charged with 40 g. of styrene monomer, 0.3 g. of sodium laurylbenzenesulfonate (hereinafter referred to as NaDBS), 0.04 g. of potassium persulfate (hereinafter referred to as KPS) and 100 g. of water, and emulsion polymerization was carried out at a reaction temperature of 70° C. After the reaction had been completed, the reaction mixture was subjected to centrifugal sedimentation at 6,000 r.p.m. for 30 minutes. The resultant particulate polymer with an average particle diameter of 0.75 micron was dispersed in glycine-NaCl buffer of pH 8.4 to obtain a latex containing 1% by volume of polystyrene.

Latex No. 3

A reaction vessel was charged with 40 g. of styrene monomer, 0.24 g. of sodium laurylsulfate (hereinafter referred to as NaLS), 0.02 g. of KPS and 100 g. of water and emulsion polymerization was carried out under the same conditions as for Latex No. 2. After the reaction had been completed, 0.8 g. of Pluronic F-68 (Wyandotte Chemical Corporation, U.S.A.) was added. After 3 hour' stirring at room temperature, the polystyrene particles were centrifuged at 6,000 r.p.m. for 30 minutes and redispersed in glycine-NaCl buffer of pH 8.4 to obtain a latex containing 1% by volume of the polystyrene particles with an average particle diameter of 0.8 micron.

Latex No. 4

Except that the NaLS of Latex No. 3 was replaced with 0.3 g. of NaDBS and the Pluronic F-68 added after the reaction was replaced with 1.0 g. of Emulsit L 16 (Dai-ichi Kogyo Seiyaku, Japan), the procedure described for Latex No. 3 was repeated to prepare a latex.

Latex No. 5

A reaction vessel was charged with 100 g. of styrene monomer, 1 g. of KPS and 150 g. of water and, in an atmosphere of nitrogen gas, polymerization reaction was carried out at 70° C. After 15 hours of reaction, there was obtained a latex of particulate polystyrene with an average particle diameter of 0.71 micron.

After the reaction, 100 g. of a 1% (by weight) solution of Pluronic F-68 was added to the above latex which was then allowed to stand at room temperature for 3 hours. The latex was then centrifuged at 6,000 r.p.m. for 30 minutes and the sedimented polystyrene particles were redispersed in glycine-NaCl buffer of pH 8.4 to obtain a latex containing 1% by volume of the polystyrene particles.

Latex No. 6

A reaction vessel was charged with 56 g. of styrene monomer, 14 g. of chlorostyrene monomer, 0.75 g. of KPS and 280 g. of water and, under stirring in an atmosphere of nitrogen gas, polymerization reaction was carried out at a temperature of 70° C. After 10 hours of reaction, a latex of a homogeneous particulate copolymer of styrene and chlorostyrene was obtained. To this latex was added 140 g. of a 1% (by weight) solution of Emulsit 49 (Dai-ichi Kogyo Seiyaku, Japan) and, after stirring at room temperature for 3 hours, the latex was centifuged and the sedimented latex particles were suspended in glycine-NaCl buffer of pH 8.4 to obtain a latex containing 1% by volume of the particles with an average particle diameter of 0.6 micron.

Latex No. 7

A reaction vessel was charged with 30 g. of methyl methacrylate monomer, 0.1 g. of NaLS, 0.05 g. of KPS and 270 g. of water and, under stirring in an atmosphere of nitrogen gas, emulsion polymerization was carried out at 70° C for 4 hours. The above procedure provided a latex of particulate homopolymer of methyl methacrylate with an average particle diameter of 0.35 micron. To this latex was added 30 g. of a 2% solution of Emulsit L 36 (Dai-ichi Kogyo Seiyaku Japan) and, after stirring at room temperature for 3 hours, the latex was subjected to centrifugal sedimentation at 6,000 r.p.m. for 30 minutes. The sedimented particles were suspended in glycine-NaCl buffer of pH 8.4 so as to give a latex containing 1% by volume of the particles.

Latex No. 8

A reaction vessel was charged with 42 g. of styrene monomer, 28 g. of chlorostyrene monomer, 0.9 g. of KPS and 280 g. of water and, under stirring in atmosphere of nitrogen gas, polymerization reaction was carried out at 70° C for 6 hours to obtain a latex of particulate copolymer of styrene and chlorostyrene with an average particle diameter of 0.9 micron. To this latex was added 70 g. of a 1% (by weight) solution of Emulsit 25 (Dai-ichi Kogyo Seiyaku, Japan) and, after stirring at room temperature for 3 hours, the latex was centrifuged at 6,000 r.p.m. for 30 minutes. The sedimented particles were suspended in glycine-NaCl buffer of pH 8.4 so as to give a latex containing 1% by volume of the copolymer.

Latex No. 9

A reaction vessel was charged with 40 g. of vinyl chloride monomer, 0.8 g. of NaLS, 0.3 g. of KPS and 60 g. of water and, under stirring in atmosphere of nitrogen gas, polymerization reaction was carried out at 55° C for 20 hours to obtain a latex of particulate polyvinyl chloride with an average particle diameter of 0.35 micron. To this latex was added 80 g. of a 1% (by weight) solution of Pluronic F-68 and, after standing at room temperature for 3 hours, the latex was centrifuged. The sedimented particles were suspended in glycine-NaCl buffer of pH 8.4 so as to give a latex containing 1% by volume of the particles.

A test tube was filled with 1 volume part of one of the above-mentioned basal latices and 1 volume part of a serial dilution of human serum in glycine-NaCl buffer of pH 8.4 and, after thorough mixing, the strength of the spontaneous agglutination that had taken place at room temperature was assessed by the naked eye and under a microscope at a magnification factor of 80 times. The results are set forth below in Table 1:

Table 1

| Latex | Assessment Method | Time | Dilution of human serum (times) | | | | | | | | |
|---|---|---|---|---|---|---|---|---|---|---|---|
| | | | 5 | 10 | 20 | 40 | 80 | 160 | 320 | 640 | 1280 |
| Latex No.1 | Naked eye | After 2 hrs. | +++ | +++ | ++ | + | − | + | ++ | ++ | − |
| | | After 24 hrs. | +++ | +++ | +++ | ++ | ++ | +++ | +++ | ++ | + |
| | ×80 | After 2 hrs. | +++ | +++ | ++ | + | + | ++ | +++ | +++ | ++ |
| | | After 24 hrs. | +++ | +++ | +++ | +++ | +++ | +++ | +++ | +++ | ++ |
| Latex No.2 | Naked eye | After 2 hrs. | +++ | +++ | ++ | ++ | ++ | + | ++ | ++ | + |
| | | After 24 hrs. | +++ | +++ | +++ | ++ | +++ | ++ | ++ | +++ | ++ |
| | ×80 | After 2 hrs. | +++ | +++ | ++ | ++ | +++ | ++ | ++ | +++ | + |
| | | After 24 hrs. | +++ | +++ | +++ | ++ | +++ | ++ | ++ | +++ | ++ |
| Latex No.3 | Naked eye | After 2 hrs. | − | − | − | − | − | − | − | − | − |
| | | After 24 hrs. | + | − | − | − | − | − | − | − | − |
| | ×80 | After 2 hrs. | + | − | − | − | − | − | − | − | − |
| | | After 24 hrs. | + | + | + | − | − | − | − | − | − |
| Latex No.4 | Naked eye | After 2 hrs. | − | − | − | − | − | − | − | − | − |
| | | After 24 hrs. | − | + | − | − | − | − | − | − | − |
| Latex No.5 | Naked eye | After 2 hrs. | − | − | − | − | − | − | − | − | − |
| | | After 24 hrs. | − | − | − | ± | ± | − | − | − | − |
| Latex No.6 | Naked eye | After 2 hrs. | − | − | − | − | ± | − | − | − | − |
| | | After 24 hrs. | − | − | − | ± | ± | − | − | − | − |
| Latex No.7 | Naked eye | After 2 hrs. | − | − | − | − | − | − | − | − | − |
| | | After 24 hrs. | − | − | − | − | − | − | − | − | − |
| Latex No.8 | Naked eye | After 2 hrs. | − | − | − | − | ± | − | − | − | − |
| | | After 24 hrs. | − | − | − | ± | ± | − | − | − | − |
| Latex No.9 | Naked eye | After 2 hrs. | − | − | − | − | ± | − | − | − | − |
| | | After 24 hrs. | − | − | − | ± | ± | − | − | − | − |

Notes:
+++; Very strong agglutination.
++; Strong agglutination.
+; Moderate agglutination.
*; Weak agglutination.
−; No agglutination.
±; Trace or doubtful agglutination.
These apply to all the Tables appearing hereinafter.

As will be seen from the above results, the latex reagents according to this invention are prominently stable with a far reduced intensity of spontaneous agglutination and it was well established that these reagents are of value for diagnostic purposes.

EXAMPLE 2

Relation of the concentration of a proteinous antigen (human IgG) employed for the sensitization of polystyrene latex and the intensity profiles of the agglutination reactions induced by anti-human IgG antibodies of immunoglobulin M(IgM) and IgG types.

One volume part of a 1% polystyrene dispersion in glycine buffer of pH 8.2 was mixed with one volume part of a solution of human IgG as diluted with glycine buffer of pH 8.2 and, after standing on a water bath (37° C) for 2 hours and at 5° C for 2 days, the admixture was shaken well to prepare a homogeneous emulsion. On a hole glass, one drop of this emulsion was mixed with one drop of a 20-fold dilution by the glycine buffer of a rheumatoid arthritis patient's serum containing rheumatoid factor which is an anti-IgG antibody of IgG type, or anti-human IgG hyperimmune rabbit serum containing anti-human IgG antibody of IgM type.

After 3 minutes' shaking, the intensities of agglutination reactions were compared. The results are summarized in Table 2 below:

Table 2

| Latex | Type of antibody | Stock solution | 2-fold | 4-fold | 8-fold | 16-fold | 32-fold | 64-fold | 128-fold | 256-fold | Control (buffer only) |
|---|---|---|---|---|---|---|---|---|---|---|---|
| Latex No.1 | Rheumatoid patient's serum | ++ | ++ | ++ | ++ | ++ | + | + | + | ± | ± |
|  | Rabbit hyperimmune serum | ++ | ++ | ++ | ++ | ++ | + | * | ± | ± | ± |
|  | Control (buffer) | + | + | * | ± | ± | ± | ± | ± | ± | ± |
| Latex No.2 | Rhematoid patient's serum | ++ | ++ | ++ | ++ | ++ | + | + | + | ± | ± |
|  | Rabbit hyperimmune serum | ++ | + | + | + | * | ± | ± | − | − | ± |
|  | Control (buffer) | * | ± | ± | ± | − | − | − | − | − | ± |
| Latex No.3 | Rheumatoid patient's serum | + | + | + | + | + | ++ | ++ | + | − | − |
|  | Rabbit hyperimmune serum | ++ | + | + | + | + | − | − | − | − | − |
|  | Control (buffer) | − | − | − | − | − | − | − | − | − | − |

Notes:
*¹The solution of human IgG, the antigen, had an undiluted concentration of 10 mg/ml. This stock antigen solution was doubling-diluted. Thus, "16-fold", for instance, means the 1 % polystyrene latex was sensitized with an equal volume of an antigen solution of (10 × 1/16) mg/ml. concentration.

The range over which an intense agglutination was induced by anti-human IgG antibody of IgG type. Each solid line signifies that, in the range to its left, correct assessment unfeasible on account of spontaneous agglutination.

According to this experiment, the conventional commercial product Latex No.1 and Latex No.2 referred to Example 1 show similar reaction intensity profiles, for both IgG and IgM antibody types. In contract, in the case of Latex No.3 according to this invention, an intense agglutination takes place on sensitization with a suitable concentration of antigen when the antibody is IgG type but the agglutination tends to be inhibited by the presence of excess antigen. Against the antibody of IgM type, Latex No.3 displays an agglutination reaction intensity profile similar to the profiles of Latex No.1 and Latex No.2 and, therefore, it is possible to differentiate an anti-human IgG antibody of IgM type from an anti-human IgG antibody of IgG type by this phenomenon. It is also apparent from the above table that, even when mixed with a comparatively high concentration of proteinous antigen (human IgG in this case), Latex No.3 does not undergo spontaneous agglutination.

EXAMPLE 3

Preparation of a Highly Sensitive Serodiagnostic Reagent for Rheumatoid Arthritis An auto-antibody to human IgG exists in the serum of a patient with rheumatoid arthritis and this disease can be diagnosed by detecting this antibody (RA factor). However, the RA reagent which is commonly employed today (the polystyrene latex sensitized with human IgG) does not react adequately with the RA factor which is only weakly reactive. The result of this experiment attests to the superior sensitivity of the reagent obtained by sensitizing the latex of this invention with a comparatively high concentration of human IgG.

Aliquots of a 1 % suspension of the latex according to this invention (Latex No.3 referred to in Example 1) were respectively mixed with equal volume parts of various serial dilutions of human IgG and each mixture was allowed to stand at 37° C for 2 hours and, then, at 5° C for a day. Thereafter, the mixture was washed twice by 10 minutes, centrifugal sedimentation at 9,000 r.p.m. and subsequent redispersion into glycine buffer of pH 8.2. Thus-obtained sensitized particles were suspended in glycine buffer of pH 8.2 containing 0.01 % of NaN₃ to prepare a serodiagnostic reagent containing 0.5% by volume of the sensitized particles.

Then, the agglutination reactions thereof with several RA-positive sera of different reaction intensities and an RA-negative serum were investigated.

The results are set forth in Table 3 below. It is apparent that with increasing amounts of adsorbed (sensitized) antigen, agglutination reactions came to be induced even by the rheumatoid patients sera of weak reactivity.

Table 3

| Patient's serum, diluted 20-fold | | Dilutions of 10 mg./ml. human IgG stock solution which were used for sensitization | | | | | | |
|---|---|---|---|---|---|---|---|---|
| | | 5-fold | 10-fold | 20-fold | 40-fold | 80-fold | 160-fold | 320-fold |
| RA(+) | No.46 | +++ | +++ | ++ | ++ | * | ± | − |
| | No.47 | ++ | ++ | + | ± | − | − | − |
| | No.33 | + | + | ± | − | − | − | − |
| | No.30 | * | ± | − | − | − | − | − |
| RA(−) | No.23 | − | − | − | − | − | − | − |

(Test procedure: On a hole glass, 1 drop of a 20-fold dilution of the patient's serum was mixed with 1 drop of the latex reagent and, after the mixture was shaken for 3 minutes, the agglutination was determined)

Thus, to prepare an RA reagent of high sensitivity, it is desirable to perform the sensitization procedure with the use of human IgG solution of the highest concentration within the test range but, at this concentration, Latex No.1 and Latex No.2 referred to Example 1 underwent spontaneous agglutination so that no RA reagent could be prepared.

Based on the above result, an equal volume part of Latex No.3 was sensitized with human IgG solution (concentration 2 mg./ml.) to prepare an RA reagent in the above manner and using this RA reagent and a commercial polystyrene latex reagent for rheumatoid arthritis, the sera of patients who had been clinically diagnosed to have rheumatoid arthritis were tested. The test results are summarized in Table 4 below:

Table 4

| RA reagent | Serodiagnostic date (The number of cases, and percents) | | | |
|---|---|---|---|---|
| | Strongly positive | Moderately positive | Weakly positive | Negative |
| Commercial RA reagent | 8 (32 %) | 3 (12 %) | 9 (36 %) | 5 (20 %) |
| Latex reagent of this invention | 12 (48 %) | 6 (24 %) | 4 (16 %) | 3 (12 %) |

Thus, whereas with the commercial RA reagent, 20 % of the sera of patients with rheumatoid arthritis were judged to be RA-negative, only 12 % of these patients were judged to be RA-negative with the reagents prepared from Latex No.3 according this invention. The existence of rheumatoid arthritis that gives negative serologic reactions is well known and it is probable that the cases which do not react to the RA reagent made from Latex No.3 according to this invention substantially coincide with the cases of "sero-negative rheumatoid arthritis" in the strict sense of the term.

It should be noticed that, in the case of the RA reagent based on the latex of this invention, no nonspecific agglutination takes place against RA-negative sera even after an elapse of more than 5 to 10 minutes and, therefore, it is easier to render a judgement than with the commercial RA reagent which apts to give a fictitious result unless the reaction result is assessed within 1 to 3 minutes.

It will also be apparent from the above result that, in many instances, an intense and clear agglutination takes place even with RA-positive sera of weak reactivity and, in this respect, too, the incidence of erroneous judgement has been diminished.

EXAMPLE 4

An example of latex agglutination reaction using a latex sensitized with a secretion-type saliva in an acid buffer.

It is acknowledged that polystyrene latex adsorbs protein-and riboprotein-antigens and is agglutinated by the corresponding antibodies but does not adsorb polysaccharide antigens well and, therefore, is not strongly agglutinated by antipolysaccharide antibodies. However, a clearly positive reaction was observed when a water-soluble ABO blood type substance, one of typical polysaccharide antigens, was caused to get adsorbed on the latex of this invention and an agglutination reaction test was carried out using an acid buffer.

The saliva, immediately after collection, was heated on a water bath at 100° C for 20 minutes and allowed to cool. Then, it was subjected to contrifugal sedimentation at 12,000 r.p.m. for 15 minutes. The supernatant was collected and dialyzed against the buffer solution. This stock solution was diluted with the buffer and mixed with an equal volume part of 1 % polystyrene latex (Latex No.3 redispersed in the buffer of required pH). The mixture was allowed to stand at 37° C for 2 hours and at 5° C for a day. To this was added bovine serum albumin in a final concentration of 1 % by volume and the mixture was further allowed to stand at 37° C for 2 hours and at 5° C for a day. It was then washed twice by 5 minutes' centrifugal sedimentation at 9,000 r.p.m. and redispersion in buffer, and dispersed in a buffer containing bovine serum albumin in a final concentration of 1%. The dispersion was filtered through a filter paper to prepare a test reagent. As buffers, use were made of a glycine buffer of pH 8.2 (glycine-NaOH buffer) and a glycine buffer of pH 3.5 (glycine-HCl buffer) for all the operations of sensitization, washing and redispersion. The anti-A or anti-B agglutinin serum was then permitted to act on each of these polystyrene latices sensitized with human saliva and the relation of the factors of dilution of saliva used for the sensitization of polystyrene (based on the volume of stock saliva) with the titers of agglutinin was determined.

Thus, in this experiment, the latex of this invention sensitized with AS saliva was agglutinated by anti-A serum alone and the latex sensitized with BS saliva was only agglutinated by anti-B serum. Therefore, there was no specificity problem. As to potency, it was considerably higher where a glycine-HCl buffer of pH 3.5 was employed.

In the case of Latex No.2, it was agglutinated on mere dispersion in the buffer of pH 3.5 and, even in the case of pH 8.2, the latex underwent spontaneous agglutination at the stage of mixing with saliva in the aforementioned sensitizing operation and the agglutination was not reversed by the subsequent steps of sensitization. Therefore, this product could not be used in tests with agglutinin sera.

Table 5

| Type of polystyrene latex buffer | pH of saliva (*) | ABO groups and Ss System of tinin | Type of agglu- 2 | \multicolumn{8}{c}{Dilutions of saliva used for sensitization of polystyrene latex} |
|---|---|---|---|---|---|---|---|---|---|---|---|
| | | | | 4 | 8 | 16 | 32 | 64 | 128 | 256 | (buffer) Control |
| No. 3 | 3.5 | AS | Anti-A | 8 | 8 | 16 | 16 | 8 | 4 | 2 | 0 | 0 |
| | | | Anti-B | 0 | 0 | 0 | 0 | 0 | 0 | 0 | 0 | 0 |
| | | BS | Anti-A | 0 | 0 | 0 | 0 | 0 | 0 | 0 | 0 | 0 |
| | | | Anti-B | 4 | 8 | 16 | 32 | 16 | 8 | 4 | 2 | 0 |
| | | AS | Anti-A | 1 | 1 | 0 | 0 | 0 | 0 | 0 | 0 | 0 |
| | | | Anti-B | 0 | 0 | 0 | 0 | 0 | 0 | 0 | 0 | 0 |
| | | BS | Anti-A | 0 | 0 | 0 | 0 | 0 | 0 | 0 | 0 | 0 |
| | | | Anti-B | 1 | 0 | 0 | 0 | 0 | 0 | 0 | 0 | 0 |
| | 8.2 | AS | Anti-A | 2 | 1 | 1 | 1 | 1 | 0 | 0 | 0 | 0 |
| | | | Anti-B | 0 | 0 | 0 | 0 | 0 | 0 | 0 | 0 | 0 |
| | | BS | Anti-A | 0 | 0 | 0 | 0 | 0 | 0 | 0 | 0 | 0 |
| | | | Anti-B | 0 | 1 | 1 | 0 | 0 | 0 | 0 | 0 | 0 |
| | | AS | Anti-A | 0 | 0 | 0 | 0 | 0 | 0 | 0 | 0 | 0 |
| | | | Anti-B | 0 | 0 | 0 | 0 | 0 | 0 | 0 | 0 | 0 |
| | | BS | Anti-A | 0 | 0 | 0 | 0 | 0 | 0 | 0 | 0 | 0 |
| | | | Anti-B | 0 | 0 | 0 | 0 | 0 | 0 | 0 | 0 | 0 |
| No.2 | 8.2 | AS | Anti-A | \multicolumn{8}{l}{No test was possible due to non-specific aggultination} |
| | | | Anti-B | | | | | | | | |
| | | BS | Anti-A | \multicolumn{8}{l}{No test was possible due to non-specific aggulatination.} |
| | | | Anti-B | | | | | | | | |
| | | AS | Anti-A | \multicolumn{8}{l}{No test was possible due to non-specific agglutination.} |
| | | | Anti-B | | | | | | | | |
| | | BS | Anti-A | \multicolumn{8}{l}{No test was possible to non-specific agglutination.} |
| | | | Anti-B | | | | | | | | |

(*) S=secretion-type; s=non-secretion type
The figures in the table stand for agglutinin titers; "1" means that reactions occur only with undiluted agglutinin serum; "0" means that no reactions induced even by undiluted agglutinin serum.

EXAMPLE 5

Sensitization of the Latex with Australia Antigen

Australia antigen (hepatitis-associated antigen, transfusion-associated hepatis virus) is well adsorbed on polystyrene latex, but to ensure an intense agglutination by Australia antibody, it is preferable to have a large amount of Australia antigen adsorbed on the polystyrene latex.

Since Latex No.1 and Latex No.2 underwent spontaneous agglutination upon admixture with sera containing Australia antigen when the serum concentration was high, they could be mixed only with highly diluted sera (100 to 150-fold or more dilutions).

In contrast, the latex according to this invention did not undergo spontaneous agglutination upon admixture with a 10-fold dilution of human serum containing Australia antigen and, therefore, it was possible to prepare from it a latex reagent which can exhibit well-defined agglutination. The following is an exemplary procedure for the preparation of such a reagent.

A human serum containing Australia antigen was diluted ten-fold with the glycine buffer of pH 8.2 and subjected to centrifugal sedimentation at 12,000 r.p.m. for 15 minutes. The supernatant was separated and mixed with an equal volume part of Latex No.3. The mixture was stored at 37° C for 2 hours, after which time bovine serum albumin was added to give a final concentration of 1 %. Finally NaN$_3$ was added in a final concentration of 0.1 %. The system was allowed to stand at 5° C for 4 days and, then, filtered. This reagent was used for detecting Australia antigen. It retained its reactivity stably for more than a year, during which period no spontaneous agglutination was encountered.

The test with this reagent is performed in the following manner: Thus, one drop of the human serum to be tested and one drop of the reagent are dripped into a small test tube and, after the two have been sufficiently mixed together with shaking, the contents are subjected to centrifugal sedimentation at 2,500 r.p.m. for 30 minutes and investigated for positive or negative agglutination. The positive agglutination is considered to be indicative of the presence of Australia antigen.

EXAMPLE 6

An example of application as a reagent for antigen-antibody reactions in the presence of fibrinogen (Detection of haptoglobin in plasma).

Fibrinogen is the most easily precipitatable of all the plasma proteins, and polystyrene latex particles are non-specifically agglutinated by its presence.

In the case of Latex No.1 and Latex No.2, such non-specific agglutinations took place at fibrinogen concentrations not less than 0.1 mg./ml. Latex No. 4, on the other hand, underwent agglutination at concentrations not less than 2 to 5 mg./ml. Therefore, when a polystyrene latex having an anti-plasma protein antibody absorbed thereon is to be reacted for the detection of plasma proteins, the Latex No. 4 according to this invention is appropriate.

The exemplary detection of haptoglobin, one of plasma proteins, was carried out in the following manner:

An anti-human haptoglobin precipitin serum was diluted 50-fold with a glycine buffer of pH 8.2 and subjected to centrifugal sedimentation at 12,000 r.p.m. for 15 minutes. The supernatant was mixed with an equal volume part of Latex No. 4 and the mixture was allowed to stand at 37° C for 2 hours and, then, at 5° C for 4 days. It was subjected to centrifugal sedimentation at 9,000 r.p.m. for 5 minutes to precipitate the latex particles and, after the supernatant was discarded, the particles were resuspended in glycine buffer of pH 8.2 containing 0.1% of NaN$_3$. This reagent underwent no non-specific agglutination with a 20-fold dilution of plasma. On a glass plate, one drop of a 20-fold dilution of human serum was mixed with 1 drop of this reagent and the mixture was visually inspected for 2 minutes while the glass plate was, in a way, rotated. The latex underwent agglutination when the plasma contained haptoglobin, while no agglutination took place in the case of haptoglobin-free plasma.

EXAMPLE 7

An example of quantitative agglutination reaction by the microtitration technique using the latex sensitized rabbit Ig G.

Latex No. 8 was mixed with equal volume part of glycine buffer of pH 8.2 containing 1.0% by volume of purified rabbit Ig G and the mixture was allowed to stand at 37° C for 2 hours and, then, at 5° C for 2 days. Thereafter, the mixture was washed twice by 15 minutes centrifugation at 4,000 r.p.m. and subsequent redispersion into glycine buffer of pH 8.2. Thus-sensitized particles were suspended in glycine buffer of pH 8.2 containing 0.1% by weight of $NaN_3$ to obtain a latex reagent containing 0.3% by volume of the sensitized particles.

Using the thus-prepared reagent, the anti-rabbit Ig G titer of the subject sera listed in Table 6 below was determined in the following manner:

The subject serum was diluted with glycine buffer of pH 8.2 by serial two-fold dilutions, and the dilution series were put in a microtiter plate at one each drop (about 0.025 ml.) per hole. One drop (about 0.025 ml.) of the latex reagent was added to each hole of the microtiter plate. After shaking, the microtiter plate was kept standing at room temperature for 4 hours, and then examined for the emergence of agglutination clumps in the conventional manner described e.g. in "Journal of Immunology", 88, 320–329 (1962). The titer of anti-rabbit Ig G antibody was determined as the reciprocal number of the highest dilution of the subject serum for exhibiting an agglutination clump with the latex reagent.

The results are summarized in Table 6 below:

Table 6

| Clinical diagnosis | Serum No. | Anti-rabbit Ig G titer Ig G titer |
|---|---|---|
| Rheumatoid arthritis patients | 1 | 256 |
| | 2 | 128 |
| | 3 | 512 |
| | 4 | 256 |
| | 5 | 128 |
| Normal or patients other than rheumatoid arthritis | 6 | 32 |
| | 7 | 16 |
| | 8 | 16 |
| | 9 | 32 |

A subject whose serum gives a titer of 64 or higher by the above-mentioned test can be serologically diagnosed as a rheumatoid arthritis patient.

The foregoing Examples 1 through 7 are intended to illustrate only a part of the broad applicability of the latex reagent of this invention to a variety of serologic reactions and it is to be understood that the present latex reagent can be employed with advantage for a large variety of serologic reactions per se known as described in, e.g. pp. 374–440 of "Methodology of Immunochemical and Immunological Research" written by J.B.G. Kwapinski et al. and published by Wiley-Interscience, New York, in 1972.

What is claimed is:

1. A method for preparing a latex reagent for serologic reactions, which comprises allowing latex particles to adsorb a nonionic surfactant, sensitizing the latex particles with an antigen or antibody and suspending the sensitized latex particles in an aqueous solvent, said nonionic surfactant being selected from the group consisting of a block copolymer of ethylene oxide and polyoxypropylene glycol which contains, within it's respective molecules, about 50% to about 80% of ethylene oxide, with the molecular weight of the hydrophobic polyoxypropylene glycol units being about 950 to about 3,850; a polyoxyethylene alkyl ether containing about 30 moles to about 100 moles of ethylene oxide and wherein the alkyl group contains 12 to 18 carbon atoms; and a polyoxyethylene alkylaryl ether which contains about 30 moles to about 100 moles of ethylene oxide and wherein the alkylaryl is phenyl substituted with alkyl of 8 to 18 carbon atoms.

2. The method of claim 1, wherein the latex particles are of a synthetic resin.

3. The method of claim 2, wherein the synthetic resin is a homopolymer or copolymer of styrene, chlorostyrene, methyl methacrylate, vinyl chloride and vinylidene chloride.

4. The method of claim 1, wherein the latex particles are of polystyrene.

5. The method of claim 1, wherein the latex particles are of a copolymer of styrene and chlorostyrene.

6. The method of claim 1, wherein the latex particles are of diameter falling within the range of from about 0.1 to about 1 micron.

7. The method of claim 1, wherein the adsorption is carried out by contacting the latex particles with the surfactant in an aqueous medium.

8. The method of claim 1, wherein the surfactant is adsorbed on the latex particles in an amount of from about 0.00001 to about 5% by weight relative to the latex particles.

9. The method of claim 1, wherein the latex particles are sensitized with Australia antigen or a human immunoglobulin G.

10. The method of claim 1, wherein the sensitization is carried out by contacting the latex particles with the antigen or antibody in an aqueous solvent.

11. The method of claim 1, wherein the aqueous solvent is water, a physiological saline or a buffer solution.

12. The method of claim 1, wherein amount of the sensitized latex particles is in a range of from about 0.1 to about 5% by volume relative to the ultimate reagent.

13. A latex reagent for serologic reactions, which is prepared by allowing latex particles to adsorb a nonionic surfactant, sensitizing the latex particles with an antigen or antibody and suspending the sensitized latex particles in an aqueous solvent, said nonionic surfactant being selected from the group consisting of a block copolymer of ethylene oxide and polyoxypropylene glycol which contains, within it's respective molecules, about 50% to about 80% of ethylene oxide, with the molecular weight of the hydrophobic polyoxypropylene glycol units being about 950 to about 3,850; a polyoxyethylene alkyl ether containing about 30 moles to about 100 moles of ethylene oxide and wherein the alkyl group contains 12 to 18 carbon atoms; and a polyoxyethylene alkylaryl ether which contains about 30 moles to about 100 moles of ethylene oxide and wherein the alkylaryl is phenyl substituted with alkyl of 8 to 18 carbon atoms.

14. The latex reagent of claim 13, wherein the latex particles are made of a synthetic resin.

* * * * *